(12) United States Patent
Guo et al.

(10) Patent No.: US 11,796,668 B2
(45) Date of Patent: Oct. 24, 2023

(54) RADAR DETECTION AND IDENTIFICATION DEVICE

(71) Applicant: ioNetworks INC., New Taipei (TW)

(72) Inventors: Jing-Ming Guo, New Taipei (TW); Ting Lin, New Taipei (TW); Chia-Fen Chang, New Taipei (TW); Jeffry Susanto, New Taipei (TW); Yi-Hsiang Lin, New Taipei (TW); Po-Cheng Huang, New Taipei (TW); Yu-Wen Wei, New Taipei (TW)

(73) Assignee: IONETWORKS INC., New Taipei (TW)

( * ) Notice: Subject to any disclaimer, the term of this patent is extended or adjusted under 35 U.S.C. 154(b) by 338 days.

(21) Appl. No.: 17/218,106

(22) Filed: Mar. 30, 2021

(65) Prior Publication Data

US 2022/0317280 A1 Oct. 6, 2022

(51) Int. Cl.
*G06K 9/20* (2006.01)
*G06K 9/62* (2022.01)
*G01S 13/86* (2006.01)
*G01S 7/06* (2006.01)
*G06V 40/16* (2022.01)

(52) U.S. Cl.
CPC .............. *G01S 13/867* (2013.01); *G01S 7/06* (2013.01); *G06V 40/172* (2022.01)

(58) Field of Classification Search
CPC ................. G01S 13/867; G06V 40/16–40/179
See application file for complete search history.

(56) References Cited

U.S. PATENT DOCUMENTS

| 10,898,999 B1* | 1/2021 | Cohen ..................... B25J 9/0003 |
| 2021/0045697 A1* | 2/2021 | Wang ...................... G06V 40/15 |
| 2022/0163650 A1* | 5/2022 | Min ....................... G06V 40/172 |

* cited by examiner

*Primary Examiner* — Brian Werner
(74) *Attorney, Agent, or Firm* — Chun-Ming Shih; LANWAY IPR SERVICES

(57) ABSTRACT

A radar detection and identification device is disclosed, comprising at least one display host, at least one camera and at least one radar detector, wherein the camera and the radar detector, after photographing and detecting, are capable of performing masked face recognition and radar physiological detection recognition processes in order to identify the identity information and human physiological signals and display them on the display host.

3 Claims, 4 Drawing Sheets

RADAR DETECTION AND IDENTIFICATION DEVICE

BACKGROUND OF THE INVENTION

1. Field of the Invention

The present invention relates to a radar detection and identification device capable of recognizing the identity information of the masked human faces and detecting the human body physiological signals.

2. Description of Related Art

It is globally known that the new-typed coronavirus (COVID-19) epidemic continues to spread in different counties, and among the 10 major symptoms announced by the WHO, "fever" is the most common one and 87.9% of infected people may have higher body temperatures. While other symptoms, e.g., sore throat, fatigue, general weakness, loss of smell and taste senses, etc., may be comparatively more difficult to be appreciated from observing general external characteristics. It should be noticed that, unlike traditional influenza, COVID-19 is often accompanied by symptoms such as dyspnea and shortness of breath, so physiological sensing (e.g., respirations, heart rhythms) and remote body temperature sensing have now become more feasible approaches for practical epidemic prevention operations and economic cost considerations.

In addition, the contact measurement may cause the risk of contact infection exposures, so the non-contact measurement has become the solution to the current pain points of epidemic prevention; besides, according to the current regulations, the Taiwan High Speed Rail, Taiwan Railway, highway traffic system and post office are also required to measure passengers' body temperature and confirm to wear masks during the epidemic period. Even in schools, most of them are also in cooperation with legally required epidemic prevention measures and start to take body temperature and wear masks.

Therefore, it can be seen that the above-said needs will continue to exist before the end of the epidemic. As such, in order to achieve the purposes of access controls, attendance appraisals and personnel health protections, it is desirable that high-definition cameras and radar equipment can be effectively utilized to accurately measure various physiological indices of personnel appearing in a target area, thereby avoiding the risk of personnel infection exposures caused by the direct contact measurement, and additionally in combination with the face recognition of the radar Vital Sign mask for locating people, confirming their physiological indices (e.g., regarding to shortness of breath) and weather the mask has been worn or not, such that it is possible to successfully prevent the epidemic infection issues; accordingly, the present invention can be the best solution.

SUMMARY OF THE INVENTION

The present invention discloses a radar detection and identification device, comprising at least one display host, at least one camera and at least one radar detector, wherein the camera and the radar detector are installed on any side or in the surrounding area of the display host, and the camera can photograph at least one media file and identify the identity information, and the radar detector can detect the radar wave data and convert into the human body physiological signal information, and then the identity information and the human body physiological signal information are displayed on the display host.

More specifically, the aforementioned human body physiological signal information includes the information about the number of breaths and heartbeats per minute.

More specifically, the aforementioned radar detection and identification device is further electrically connected to a server equipment which includes at lease one processor and at least one computer readable recording media for the storage of one or more media files and radar wave data, wherein the computer readable recording media further stores at least one application unit such that, when such processors execute such application units, the server equipment are enabled to perform the following procedures: in the activated application unit, the media files are identified as the identity information and the radar wave data are converted into the human physiological signal information; after that, the identity information and the human physiological signal information then are transferred to the display host and displayed.

More specifically, the aforementioned application unit includes: an input module, used to input one or more media files and radar wave data; an identity information archiving module, used to build plural identity information; a human face archiving module, connected to the identity information archiving module for building multiple masked human face images, in which different human face images respectively correspond to different identity information; a human face recognizing module, connected to the input module and the human face archiving module for recognizing whether the media files belong to the human face images already stored therein and selecting the corresponding identity information based on the recognized human face images; a radar wave processing module, connected to the input module for waveform-processing the radar wave data and then converting them into human physiological signal information; and an information output module, connected to the human face recognizing module and the radar wave processing module for transferring the obtained identity information and human physiological signal information to the display host to display.

More specifically, the aforementioned radar detector applies the millimeter wave radar technology for detection.

DETAILED DESCRIPTION OF THE PREFERRED EMBODIMENTS

Other technical contents, aspects and effects concerning the present invention can be clearly appreciated through the detailed descriptions on the preferred embodiments of the present invention in conjunction with the appended drawings.

Figure 1:
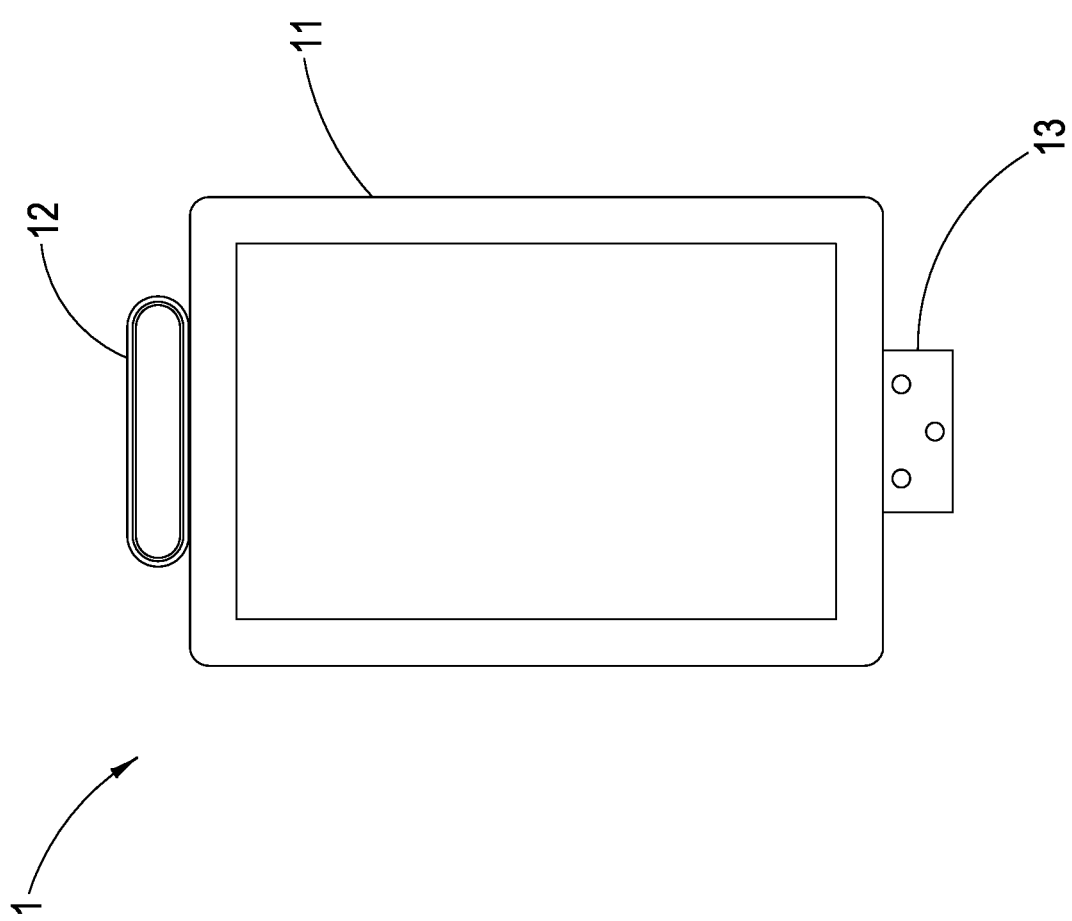
FIG. 1 shows a device view of the radar detection and identification device according to the present invention.
Figure 2:
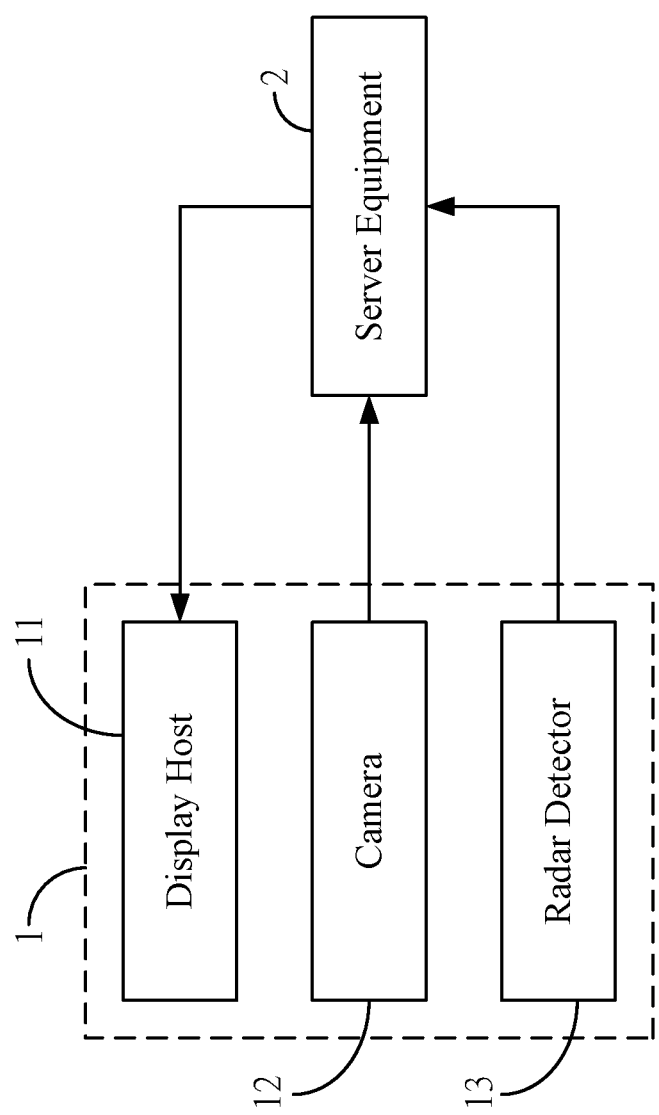
FIG. 2 shows an architecture view of the radar detection and identification device according to the present invention.
Figure 3:
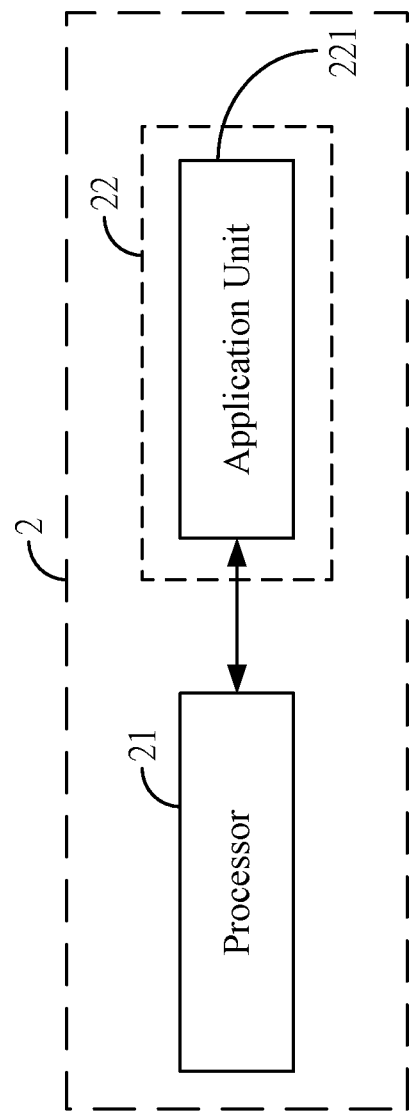
FIG. 3 shows an architecture view of the server equipment connected to the radar detection and identification device according to the present invention.
Figure 4:
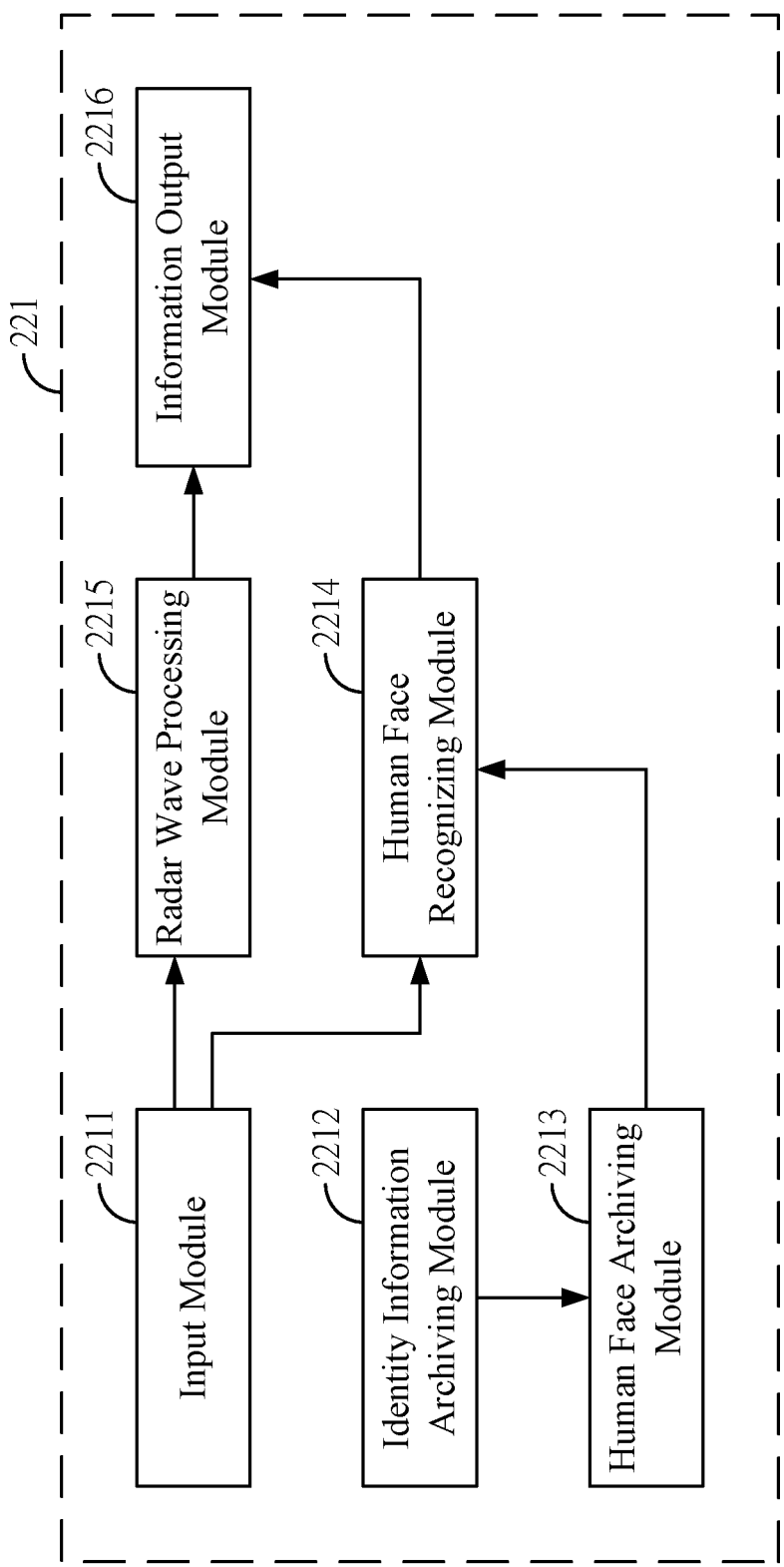
FIG. 4 shows an architecture view of the applications loaded in the server equipment connected to the radar detection and identification device according to the present invention.

Refer first to FIGS. 1-4, wherein a device view, an architecture view, an architecture view of the connected server equipment and an architecture view of the applications loaded in the connected server equipment of the radar detection and identification device according to the present invention are respectively shown. As shown in FIG. 1, the illustrated radar detection and identification device 1 according to the present invention comprises at least one display host 11, at least one camera 12 and at least one radar detector 13, wherein the camera 12 and the radar detector 13 are installed on any side or in the surrounding area of the display host 11, and the camera 12 can photograph at least one media file and identify the identity information, and the radar detector 13 can detect the radar wave data and convert into the human body physiological signal information (e.g., the information about the number of breaths and heartbeats per minute), and then the acquired identity information and human body physiological signal information are displayed on the display host 11.

In addition, the present invention effectively applies the features of millimeter wave radar: the delay between transmission and reflection signals, calculating the distance between the system and the object; meanwhile, confirming the speed of the object by measuring the corresponding phase difference. Also, the high-performance radar system can track multiple targets moving at different speeds and trajectories, and because of its useful features, e.g., wide detection range, high accuracy, and weather resistance etc, it can be utilized as the cornerstone of many applications. Moreover, by using the uniquely developed cardiac pace and breath sensing algorithm, the non-contact, 24-hour monitoring features of the present invention can be best used for integrated application purposes in multiple fields, such as medical treatment facilities, long-term care centers and smart homes or the like.

Regarding to the masked human face recognition, it is explained as below:
(1) Herein the human face detection is the first and non-negligible step in the human face recognition process, and the purpose of the human face detection model is to detect human faces in photos and image streams. Therefore, it can be understood that its input is the RGB image, and its output is the data combination of the face coordinates, a.k.a. the Regions of Interests (ROIs).
(2) The present invention uses the latest technology (applying the WIDER Face (Hard) data set) model for human face detections, e.g., RetinaFace, a powerful human face detection model capable of running simultaneously pixel-leveled face detections via the autonomous learning function.
(3) Accordingly, the present invention uses image recognition technologies, collects various archived images with and without masks, and designs two major scenarios of "correctly worn" and "not-correctly worn", as well as multiple image data, in order to facilitate the computer determination process. That is, it combines the human face recognition system thereby accurately determining whether the target object correctly wears a mask.

In order to execute the masked human face recognition and human physiological signal information recognition processes, the radar detection and identification device 1 is electrically connected to a server equipment 2 which includes at lease one processor 21 and at least one computer readable recording media 22 which stores one or more media files and radar wave data, wherein the computer readable recording media 22 further stores at least one application unit 221 such that, when such processors 21 execute such application units 221, the server equipment 2 are enabled to perform the following procedures: in the activated application unit 221, the media files are identified as the identity information and the radar wave data can be converted into the human physiological signal information; after that, the identity information and the human physiological signal information then are transferred to the display host and displayed.

Herein the application unit 221 includes:
(1) an input module 2211, used to input one or more media files and radar wave data;
(2) an identity information archiving module 2212, used to build plural identity information and store them as plural identity information files;
(3) a human face archiving module 2213, connected to the identity information archiving module 2212 to build various human face images with and without masks (at least distinguished between three scenarios with respect to the mask: correctly worn, not correctly worn and not worn), in which different human face images correspond to different identity information, and the built human face images will be respectively stored in the corresponding identity information file;
(4) a human face recognizing module 2214, connected to the input module 2211 and the human face archiving module 2213 for recognizing whether the media files belong to the human face images already stored therein (mainly used to determine the human face area not covered by the mask) and selecting the corresponding identity information based on the recognized human face images;
(5) a radar wave processing module 2215, connected to the input module 2211 for waveform-processing the radar wave data and then converting them into human physiological signal information;
(6) an information output module 2216, connected to the human face recognizing module 2214 and the radar wave processing module 2215 for transferring the obtained identity information and human physiological signal information to the display host 11 to display.

In addition, the implemented application of the radar detection and identification device 1 according to the present invention is now described as follows:
(1) The radar detection and identification device 1 first takes a certain amount of pictures to users and transfers the obtained pictures to the server equipment 2 for performing the verification process (Step 101);
(2) Performing the verification determination process (Step 102), including the following different situations:
(a) If the server equipment 2 sends back a response of verification failure or permission not matched, then a result of verification failure or permission not matched will be shown on the display host 11 (e.g., the screen stays for a certain duration of time and automatically closes), and returns to Step 101;
(b) If the user does not wear a mask or does not correctly wear a mask, a screen showing that the mask is not worn will be displayed on the display host 11 (the screen stays for a certain duration of time and automatically closes), and returns to Step 101;
(c) If the server equipment 2 completes the verification process successfully, the screen showing the radar detection is ongoing will be displayed on the display host 11, and then the radar detector 13 will be activated thereby collecting radar data (Step 103);

(3) Determining whether the user leaves the radar detection and identification device 1 within a certain duration of time (Step 104), including the following different situations:
  (a) If, after activating the radar detector 13, the same employee number (identity information) are not received within a short period of time or otherwise the received employee number is different from the current employee number, then the collected radar data will be directly sent back to the server equipment 2, instead of being shown on the display host 11 (that is, returning the reasonable radar data, which are the arithmetic averages between their multiple number intervals), and returns to Step 101;
  (b) If, after activating the radar detector 13, the user does not leave the radar detection and identification device 1 within a certain period of time, then the collected radar data will be displayed on the display host 11 and the radar data will be sent back to the server equipment 2 as well (that is, returning the reasonable radar data, which are the arithmetic averages between their multiple number intervals), and returns to Step 101.

Furthermore, the data allowed to be displayed on the display host 11 may include:
  (1) Verification result status
  (2) Greeting texts
  (3) User's name
  (4) User's employee number
  (5) User's picture
  (6) Identity color
  (7) Mask condition (0: normal, 1: not worn or not correctly worn)
  (8) Breath rate and heartbeat rate
  (9) Detection condition (0: detection completed, 1: insufficient time for data collections)

Furthermore, the present invention allows to set up the breath range (e.g., 10~25 breaths/minute) and heartbeat range (40~120 beats/minute) in order to define reasonable radar data standards, and in case the results do not fall within such defined standard ranges, a warning message may be displayed on the display host 11 or an alarm audio may be played with a speaker.

Compared with other conventional technologies, the radar detection and identification device according to the present invention provides the following advantages:
  (1) The present invention allows to accurately measure various physiological indices of people appearing in a target area by means of the high-definition camera and radar equipment, thus preventing the risk of personnel infection caused by direct contact measurement.
  (2) The present invention applies the uniquely developed cardiac pace and breath sensing algorithm and non-contact, 24-hour monitoring features to be best used for integrated application purposes in multiple fields, such as medical treatment facilities, long-term care centers and smart homes or the like.
  (3) The present invention combines the radar Vital Sign masked human face recognition for correctly locating person, confirming various physiological indices (e.g., whether the situation of short breath occurs) and whether a mask is appropriately worn, in order to achieve the goal of preventing epidemic infection.
  (4) The present invention adopts the radar Vital Sign masked human face recognition and allows to quickly notify the epidemic prevention unit in case of abnormal conditions. With respect to potential specific objects, other tracking solutions, such as Artificial Intelligence (AI) image monitoring, real-name ticket purchase system and mobile phone locating function etc. can be conjunctively applied; if a patient is confirmed to be positive, the influenced area can be quickly locked, and people who may have been in contact with the confirmed patient can be notified to notice their physical conditions and seek medical attention as soon as possible.
  (5) The present invention is mainly used for recognizing masked human faces and mask recognition technologies; therefore, compared with traditional human face recognition methods, the technologies of the present invention focus more on facial characteristics recognition between the eyes so as to accurately recognize human faces wearing masks.

It should be noticed that, although the present invention has been disclosed through the detailed descriptions of the aforementioned embodiments, such illustrations are by no means used to restrict the scope of the present invention; that is, skilled ones in relevant fields of the present invention can certainly devise any applicable alterations and modifications after having comprehended the aforementioned technical characteristics and embodiments of the present invention without departing from the spirit and scope thereof. Hence, the scope of the present invention to be protected under patent laws should be delineated in accordance with the claims set forth hereunder in the present specification.

What is claimed is:

1. A radar detection and identification device electrically connected to a server equipment, comprising at least one display host, at least one camera and at least one radar detector, wherein the camera and the radar detector are installed on any side or in the surrounding area of the display host, and the camera can photograph at least one image comprising a human face, and the image is then transferred to the server equipment to identify the identity information of the human face, and the radar detector can detect the radar wave data and convert into the human body physiological signal information, and then the identity information and the human body physiological signal information are displayed on the display host; and wherein the server equipment includes at least one processor and at least one computer readable recording media for the storage of one or more images comprising human faces and radar wave data, and the computer readable recording media further stores at least one application unit such that, when such processors execute such application units, the server equipment are enabled to perform the following procedures: in the activated application unit, the input image is identified as the identity information and the radar wave data are converted into the human physiological signal information; after that, the identity information and the human physiological signal information then are transferred to the display host and displayed; and wherein the application unit includes:
  an input module, used to input the images and radar wave data;
  an identity information archiving module, used to build plural identity information;
  a human face archiving module, connected to the identity information archiving module for building multiple masked human face images, in which different human face images respectively correspond to different identity information;
  a human face recognizing module, connected to the input module and the human face archiving module for recognizing whether the input images belong to the human face images already stored therein and selecting the corresponding identity information based on the recognized human face images;

a radar wave processing module, connected to the input module for waveform-processing the radar wave data and then converting them into human physiological signal information; and an information output module, connected to the human face recognizing module and the radar wave processing module for transferring the obtained identity information and human physiological signal information to the display host to display.

2. The radar detection and identification device according to claim 1, wherein the human body physiological signal information includes the information about the number of breaths and heartbeats per minute.

3. The radar detection and identification device according to claim 1, wherein the radar detector applies the millimeter wave radar technology for detection.

* * * * *